(12) United States Patent
Chen et al.

(10) Patent No.: US 10,981,165 B2
(45) Date of Patent: Apr. 20, 2021

(54) DEVICE AND METHOD FOR VISUAL QUANTIFICATION OF AN AMOUNT OF TARGET SPECIES IN A SAMPLE SOLUTION

(71) Applicant: City University of Hong Kong, Kowloon (HK)

(72) Inventors: Ting-Hsuan Chen, Kowloon Tong (HK); Zichen Zhao, Kowloon Tong (HK)

(73) Assignee: City University of Hong Kong, Kowloon (HK)

( * ) Notice: Subject to any disclaimer, the term of this patent is extended or adjusted under 35 U.S.C. 154(b) by 105 days.

(21) Appl. No.: 15/969,877

(22) Filed: May 3, 2018

(65) Prior Publication Data
US 2019/0336967 A1 Nov. 7, 2019

(51) Int. Cl.
*B01L 3/00* (2006.01)
*G01N 33/20* (2019.01)

(52) U.S. Cl.
CPC ........ *B01L 3/502715* (2013.01); *G01N 33/20* (2013.01); *B01L 2300/12* (2013.01); *B01L 2400/043* (2013.01); *B01L 2400/0406* (2013.01)

(58) Field of Classification Search
CPC ....... B01L 2200/0668; B01L 2300/028; B01L 2300/0816; B01L 2300/12; B01L 2400/0406; B01L 2400/043; B01L 3/502715; B01L 3/502761; G01N 33/20
See application file for complete search history.

(56) References Cited

U.S. PATENT DOCUMENTS

| | | | |
|---|---|---|---|
| 2008/0302732 A1* | 12/2008 | Soh | B01L 3/502761 210/695 |
| 2011/0124114 A1* | 5/2011 | Ermantraut | B01L 3/50273 436/164 |
| 2013/0186174 A1* | 7/2013 | Seo | G01N 30/00 73/23.35 |
| 2014/0174160 A1* | 6/2014 | Michienzi | G01N 30/16 73/61.55 |
| 2015/0024376 A1* | 1/2015 | Ozanich | G01N 33/54333 435/5 |
| 2015/0367345 A1* | 12/2015 | Yung | B01L 3/502753 356/338 |
| 2018/0214873 A1* | 8/2018 | DeVoe | B01L 3/502753 |

* cited by examiner

*Primary Examiner* — Jennifer Wecker
(74) *Attorney, Agent, or Firm* — Renner Kenner Greive Bobaktaylor & Weber (57) ABSTRACT

A device for visual quantification of an amount of target species in a sample solution. The device includes an inlet, a separator, and a trap. The inlet is arranged to receive the sample solution. The separator in fluid communication with the inlet and arranged to separate one or more species from the sample solution. The trap is arranged downstream of the separator, in fluid communication with the separator, and arranged to trap one or more species of the sample solution. The trap is arranged such that the trapped species is visible for determination of the amount of target species in the sample solution.

22 Claims, 6 Drawing Sheets

DEVICE AND METHOD FOR VISUAL QUANTIFICATION OF AN AMOUNT OF TARGET SPECIES IN A SAMPLE SOLUTION

TECHNICAL FIELD

The invention relates to a device, and particularly but not exclusively, to a microfluidic device, for visual quantification of an amount of target species in a sample solution. The invention also relates to a method for visual quantification of an amount of target species in a sample solution.

BACKGROUND

It is known important to detect and analyze target chemical species in a sample for disease diagnosis, environmental monitoring and analysis, or related health- or environment-related applications. The detection and analysis usually require dedicated equipment, such as spectrometer, fluorescence microscope, thermal cycler, current meter, etc., which are cumbersome and bulky, and require electric power to operate and so are unsuitable for use in resource limited settings.

Recently, portable sensors and detectors incorporating lateral flow strips or colorimetric assays have been designed. These sensors and detectors are convenient to use. However, they may provide only qualitative results, i.e., whether there exists the target chemical species. For applications that require quantitative measurement, UV-Vis spectrometer or lateral flow strip reader is still required to analyze the detected signal to determine spectral absorbance to quantify the optical/fluorescence intensity, which could be a complicated process.

SUMMARY OF THE INVENTION

It is an object of the invention to address the above needs, to overcome or substantially ameliorate the above disadvantages or, more generally, to provide an improved device for visual quantification of an amount of target species in a sample solution.

In accordance with a first aspect of the invention, there is provided a device for visual quantification of an amount of target species in a sample solution. The device comprises: an inlet arranged to receive the sample solution; a separator in fluid communication with the inlet and arranged to separate one or more species from the sample solution; and a trap downstream of the separator, in fluid communication with the separator, and arranged to trap one or more species of the sample solution. The trap is arranged such that the trapped species is visible for determination of the amount of target species in the sample solution.

The sample solution with the target species is preferably a water-based solution. The sample solution may be premixed with other species such as magnetic particles with surface connectors for connecting with a linker particle, polymeric particles with surface connectors for connecting with the linker particle, linker particles, their compound, and optionally other particles or elements. The magnetic particles are preferably micro-particles, nanoparticles, etc. The polymeric particles are also preferably micro-particles, nanoparticles, etc. The linker particles for connecting with the magnetic particle and the polymeric particle may be the target species, the amount of which is to be determined. This can be considered as direct measurement. Alternatively, the target species may be provided by other particles or elements in the sample solution, which can chemically react with the linker particles. This can be considered as indirect measurement. In one example, the magnetic particles are magnetic micro-particles (MMP) that are surface functionalized with a connection probe for connection with the linker particle. In one example, the polymeric particles are polystyrene microparticles (PMP) surface functionalized with a connection probe for connection with the linker particle. The linker particles may include nucleic acid, protein, chemical compounds, or metal ions. The target species may include nucleic acids, protein, chemical compounds, or metal ions. The term "particle(s)" is used here to broadly refer to different forms of chemical element or compound.

The amount of trapped species may be correlated with, e.g., directly proportional to, the amount of the target species in the sample solution. Alternatively, the amount of trapped species may be correlated with, e.g., inversely proportional to, the amount of the target species in the sample solution. Other forms of correlation are also possible.

Preferably, the trap comprises a fluid channel with a tapered portion for trapping the one or more species. In one embodiment, the fluid channel is at least partly transparent or translucent such that the trapped species is visible, in any form or color. The trap may further comprise reference scale markings arranged along at least part of the fluid channel for indicating the amount of the trapped species or the amount of target species in the sample solution. As such, the trap may provide a fuel-gauge like display for intuitive visual quantification.

Preferably, the device further includes a source arranged to move the sample solution towards the trap. The source can be a suction source or a blowing source. The source preferably can operate without using electric power. In one embodiment, the source comprises a self-driven capillary pump.

In one embodiment, the separator may be a chemical separator, which separates one or more species from the sample solution via chemical interaction. Alternatively or additionally, the separator may be a physical separator, which separates one or more species from the sample solution via physical interaction. Preferably, the separator is a magnetic separator, which separates one or more species from the sample solution via magnetic interaction.

In a preferred embodiment, the separator comprises a fluid channel with an inlet portion in fluid communication with an upstream fluid channel downstream of the inlet; an outlet portion in fluid communication with a downstream fluid channel upstream of the trap; and a separation portion arranged between the inlet portion and the outlet portion. The fluid channel of the separator may be curved. In one embodiment, the inlet portion extends at an angle to an extension axis of the upstream fluid channel such that the separation portion is offset from the extension axis of the upstream fluid channel. Additionally, or alternatively, the outlet portion extends at an angle to an extension axis of the downstream fluid channel such that the separation portion is offset from the extension axis of the downstream fluid channel. Preferably, the extension axis of the upstream fluid channel and the extension axis of the downstream fluid channel are substantially coaxial.

Preferably, the cross section of the inlet portion at least partly increases from upstream to downstream, and the cross section of the fluid channel of the separator at least partly increases from the separation portion to the outlet portion.

The separator may further comprise a magnetic element arranged at or adjacent the separation portion for attracting and thereby separating one or more species from the sample solution. The magnetic element may include a permanent magnet, an electromagnet, etc.

Preferably, the target species include lead or lead ions.

Preferably, the fluid channels in the device are hydrophilic.

Preferably, the device is a microfluidic device and the respective fluid channels are micro-channels.

Preferably, the device is portable.

In accordance with a second aspect of the invention, there is provided a microfluidic device comprising one or more micro-channels arranged to form: an inlet arranged to receive the sample solution; at least part of a separator arranged to separate one or more species from the sample solution; and a trap downstream of the separator, in fluid communication with the separator, and arranged to trap one or more species of the sample solution for visual quantification of the amount of target species in the sample solution.

The microfluidic device may include one or more further features of the device in the first aspect. Preferably, the micro-channels are hydrophilic.

In accordance with a third aspect of the invention, there is provided a method for visual quantification of an amount of target species in a sample solution, comprising: separating, using a separator, one or more species from the sample solution; and trapping, using a trap downstream of and in fluid communication with the separator, one or more species of the sample solution. The trap is arranged such that the trapped species is visible for determination of the amount of target species in the sample solution. The method may further comprise determining the amount of target species in the sample solution based on the amount of trapped species.

The sample solution with the target species is preferably a water-based solution. The sample solution may be pre-mixed with other species such as magnetic particles with surface connectors for connecting with a linker particle, polymeric particles with surface connectors for connecting with the linker particle, linker particles, their compound (e.g. magnetic particle-linker particle-polymeric particle), and optionally other particles or elements. The magnetic particles are preferably micro-particles, nanoparticles, etc. The polymeric particles are also preferably micro-particles, nanoparticles, etc. The linker particles for connecting with the magnetic particle and the polymeric particle may be the target species, the amount of which is to be determined. This can be considered as direct measurement. Alternatively, the target species may be provided by other particles or elements in the sample solution, which can chemically react with the linker particles. This can be considered as indirect measurement. In one example, the magnetic particles are magnetic micro-particles (MMP) that are surface functionalized with a connection probe for connection with the linker particle. In one example, the polymeric particles are polystyrene micro-particles (PMP) surface functionalized with a connection probe for connection with the linker particle. The linker particles may include nucleic acid, protein, chemical compounds, or metal ions. The target species may include nucleic acids, protein, chemical compounds, or metal ions. The term "particle(s)" is used here to broadly refer to different forms of chemical element or compound.

The amount of trapped species may be correlated with, e.g., directly proportional to, the amount of the target species in the sample solution. Alternatively, the amount of trapped species may be correlated with, e.g., inversely proportional to, the amount of the target species in the sample solution. Other forms of correlation are also possible.

Preferably, the trap comprises a fluid channel with a tapered portion for trapping the one or more species. In one embodiment, the fluid channel is at least partly transparent or translucent such that the trapped species is visible, in any form or color.

Preferably, the method further comprises indicating, using reference scale markings arranged along at least part of the fluid channel, the amount of the trapped species or the amount of target species in the sample solution. This indication step may be performed as the one or more species is trapped by the trap.

Preferably, the method further includes moving, using a source, the sample solution towards the trap. The source can be a suction source or a blowing source. The source preferably can operate without using electric power. In one embodiment, the source comprises a self-driven capillary pump.

In one embodiment, the separator may be a chemical separator, which separates one or more species from the sample solution via chemical interaction. Alternatively or additionally, the separator may be a physical separator, which separates one or more species from the sample solution via physical interaction. Preferably, the separator is a magnetic separator, which separates one or more species from the sample solution via magnetic interaction.

In a preferred embodiment, the separator comprises a fluid channel with an inlet portion in fluid communication with an upstream fluid channel downstream of the inlet; an outlet portion in fluid communication with a downstream fluid channel upstream of the trap; and a separation portion arranged between the inlet portion and the outlet portion. The fluid channel of the separator may be curved. In one embodiment, the inlet portion extends at an angle to an extension axis of the upstream fluid channel such that the separation portion is offset from the extension axis of the upstream fluid channel. Additionally, or alternatively, the outlet portion extends at an angle to an extension axis of the downstream fluid channel such that the separation portion is offset from the extension axis of the downstream fluid channel. Preferably, the extension axis of the upstream fluid channel and the extension axis of the downstream fluid channel are substantially coaxial.

Preferably, the cross section of the inlet portion at least partly increases from upstream to downstream, and the cross section of the fluid channel of the separator at least partly increases from the separation portion to the outlet portion.

Preferably, the method further includes attracting and thus separating, using a magnetic element arranged at or adjacent the separation portion, one or more species from the sample solution. The magnetic element may be a permanent magnet, an electromagnet, etc.

Preferably, the method is performed at least partly using the device of the first aspect or the microfluidic device of the second aspect.

In accordance with a fourth aspect of the invention, there is provided a microfluidic chip incorporating the device of the first aspect or the microfluidic device of the second aspect.

In accordance with a fifth aspect of the invention, there is provided a device for visual quantification of an amount of lead ions in a sample solution, comprising: an inlet arranged to receive the sample solution; a separator in fluid communication with the inlet and arranged to separate one or more species from the sample solution; and a trap downstream of the separator, in fluid communication with the separator, and arranged to trap one or more species of the sample solution. The trap is arranged such that the trapped species is visible for determination of the amount of lead ions in the sample solution.

Preferably, the device is portable. The device may be the device of the first aspect or the microfluidic device of the second aspect.

BRIEF DESCRIPTION OF THE DRAWINGS

Embodiments of the invention will now be described, by way of example, with reference to the accompanying drawings in which.

DETAILED DESCRIPTION OF THE PREFERRED EMBODIMENT

Figure 1:
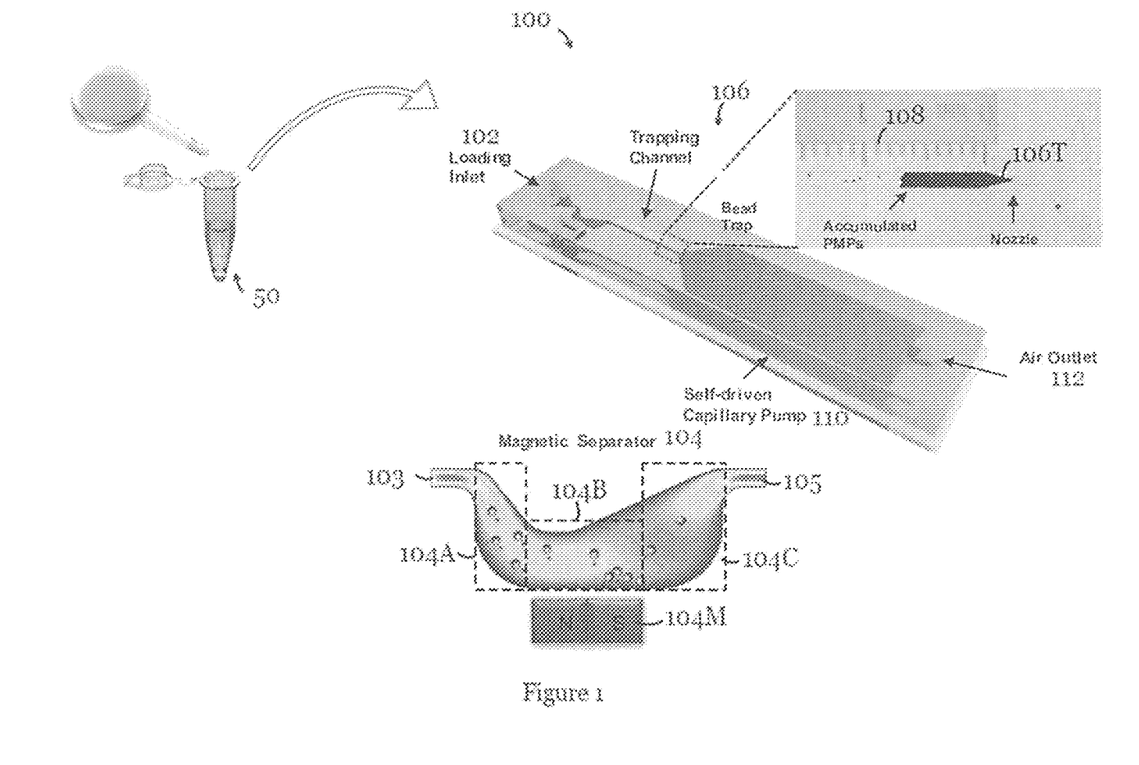
FIG. 1 is a schematic diagram of a microfluidic device for detection of an amount of target species in a sample solution in one embodiment of the invention.

Referring to FIG. 1, there is shown a microfluidic device 100, in the form of a microchip, for detection of an amount of target species in a sample solution 50. The microfluidic device 100 includes a micro-fluid channel with an inlet 102 for loading the sample solution 50. The micro-fluid channel at the inlet 102 tapers to narrow. Downstream of the inlet 102 is a magnetic separator 104 formed by a human stomach-shaped, curved channel portion with a magnet 104M arranged on a side for separating one or more species from the sample solution 50.

The magnet 104M in this embodiment is a permanent magnet. More specifically, the channel portion of the magnetic separator 104 is formed by an inlet portion 104A in fluid communication with an upstream fluid channel 103 downstream of the inlet 102, an outlet portion 104C in fluid communication with a downstream fluid channel 105 upstream of the trap 106, and a separation portion 104B arranged between the inlet portion 104A and the outlet portion 104C. The magnet 104M is arranged in a slot on a side of the separation portion 104B for attracting and thereby separating one or more species from the sample solution 50. The inlet portion 104A extends at an angle to an extension axis of the upstream fluid channel 103 such that the separation portion 104B is offset from the extension axis of the upstream fluid channel 103. The outlet portion 104C extends at an angle to an extension axis of the downstream fluid channel 105 such that the separation portion 104B is offset from the extension axis of the downstream fluid channel 105. The extension axis of the upstream fluid channel 104A and the extension axis of the downstream fluid channel 104C are substantially coaxial. The cross section of the inlet portion 102 at least partly increases from upstream to downstream, and the cross section of the channel at least partly increases from the separation portion 104B to the outlet portion 104C. Further downstream of the separator 104 is the trap 106, formed by another channel portion, for trapping one or more remaining species in the sample solution 50 that has undergone separation, i.e., with one or more species already removed. The channel portion of the trap 106 includes a tapered portion 106T, with a nozzle, for trapping one or more remaining species. The trap 106T is arranged such that the trapped species is visible for determination of the amount of target species in the sample solution 50. In particular, the trapped species accumulate in the trap 106 to form a visible bar, like a fuel-gauge display. The length of the bar formed by the trapped species is correlated with the amount of target species in the sample solution. In this example, the channel portion of the trap 106 is at least partly transparent or translucent to allow the trapped species to be visible. Reference scale markings 108 are arranged along part of the channel portion of the trap 106 for indicating the amount of the trapped species or the amount of target species in the sample solution. In this embodiment, the reference scale markings 108 are provided by a ruler-type instrument. A source 110, in the form of a self-driven capillary pump, is arranged downstream of the trap 106 to move the sample solution from the inlet 102 to the trap 106. A fluid outlet 112 through which air (anal optionally liquid) can escape is arranged downstream of the pump 110.

Figure 2:
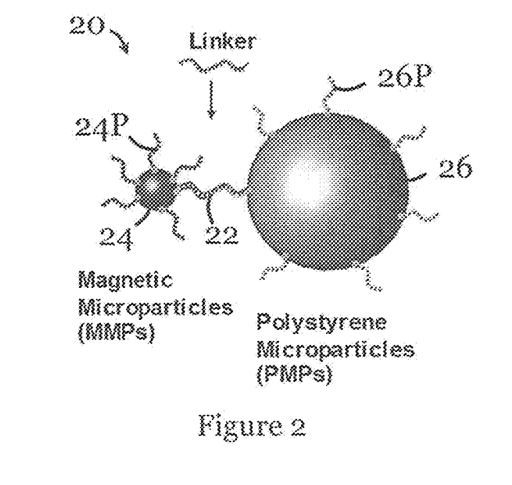
FIG. 2 is a schematic diagram of the species in the sample solution arranged to be placed in the microfluidic device of FIG. 1 in one embodiment of the invention.

FIG. 2 shows the species 20 in an exemplary sample solution arranged to be placed in the microfluidic device 100 of FIG. 1. The species 20 include a linker 22, as well as magnetic micro-particle (MMP) 24 and a polystyrene microparticle (PMP) 26, both surface-functionalized with one or more linker-binding probes 24P, 26P, and which can bind with molecular linkers 22 to form a sandwiched structure MMP-linker-PMP.

Figure 3A:
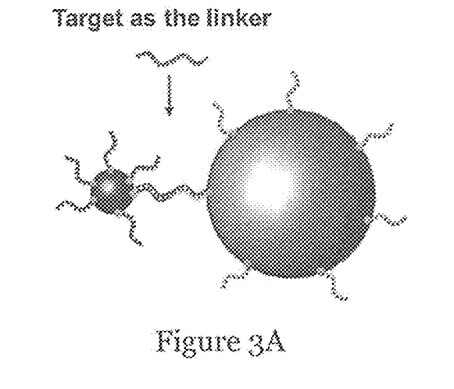
FIG. 3A is an example of the species in FIG. 2 in which the target species form the linker for direct measurement.

FIG. 3A show an example of the species in FIG. 2 in which the target species, the amount of which is to be determined, forms the linker for direct measurement. FIG.

Figure 3B:
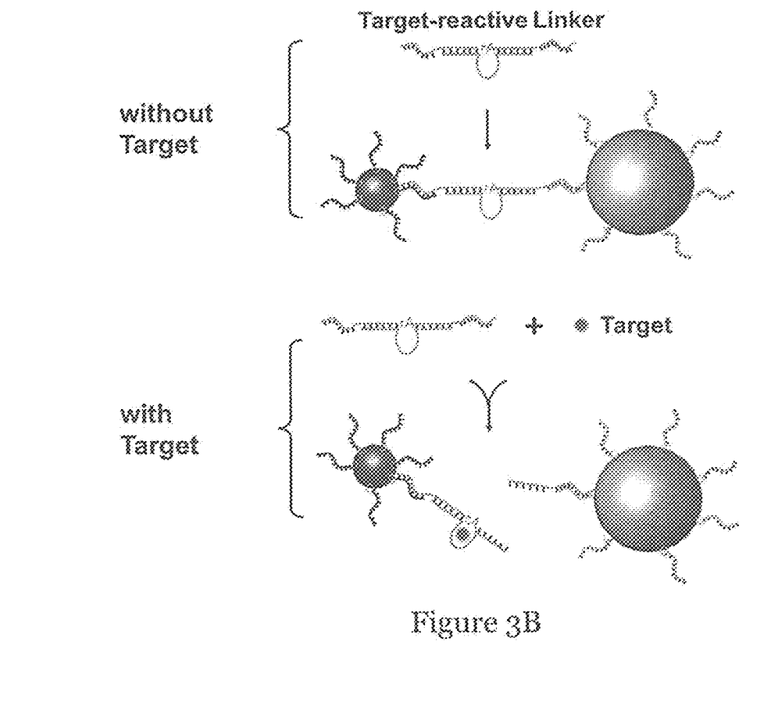
FIG. 3B is an example of the species in FIG. 2 in which the target species is arranged to react with a target-reactive linker for indirect measurement.

3B shows an example of the species in FIG. 2 in which the target species, the amount of which is to be determined, is not part of the sandwiched structure, and the linker is a target-reactive linker suitably arranged to react with the target for indirect measurement. As shown in FIG. 3B, the target species is arranged to react with the target-reactive linker to cleave the target-reactive linker. Alternatively, the target species may form or build a linker.

In operation of the device 100 of FIG. 1 using a sample solution 50 including the species 20 of FIG. 2, the solution, once loaded into the device 100 through the inlet 102, is driven by the self-driven capillary flow to move towards the trap 106. In this example, the fluid channel in the device 100 is hydrophilic so that water-based solution could spontaneously flow towards the other end, as moved by capillary force, without the need of external moving or power source. The MMPs-linkers-PMPs then pass into the magnetic separator 104, in which the MMPs-linkers-PMPs (direct measurement with target species being the linker, indirect measurement with target species building the linker) or the MMPs (indirect measurement with target species cleaving the linker) are trapped by electromagnetic interaction with the magnet 104M. By using a stomach-shape micro-channel (FIG. 1), the flow first slows down due to the expanding micro-channel at the inlet portion 104A, and the fluid stream is directly guided toward the region with strongest magnetic force in the separation portion 104B. This maximizes the capturing the MMPs-linkers-PMPs or free MMPs. After passing the region of strong magnetic field of the separation portion 104B, the micro-channel further expands to the outlet portion 104C, resulting in a slowed flow before reaching the trap 106. Efficient capturing of MMPs-linkers-PMPs or free MMPs can be achieved. Free PMPs in the solution can flow downstream and reach the trap 106. The free PMPs accumulate at the trap 106 with a tapered part 106T forming a nozzle sized to prevent downstream flow of PMPs (the width of the nozzle is less than the diameter of the PMPs). Importantly, the depth of the trapping channel of the trap 106 is arranged to be slightly larger than the diameter of PMPs such that the PMPs can be accumulated as a monolayer to maximize the visible length of PMP accumulation. The accumulation of PMPs forms a visual bar with a quantifiable length, readily observable by the naked eye, optionally with the assist of reference markings 108. The length of the bar is correlated with the amount of target species. For example, in direct measurement, the target species can be the linker such that the PMP accumulation is inversely proportional to the amount of target species. In indirect measurement, the target species can interact with the linker, e.g. forming or degrading the linker, such that the PMP accumulation is proportional to the amount of target species. During trapping, the water-based buffer solution can pass through the nozzle. Importantly, the capillary pump 110 is placed to ensure capillary attraction of liquid wicking until the capillary pump 110 is fully filled. This ensures a consistent volume filling the micro-channel, minimizing fluctuations and errors in measurement.

It should be appreciated that the connection of the species in FIG. 2 can be formed in different ways depending on the type of the linkers. For example, for direct measurement of single-strand DNA oligonucleotides, the linker-binding probes can be designed as a pair of single-strand oligonucleotides with sequences complementary to that of the target in juxtaposition. Alternatively, for direct measurement of protein, the linker-binding probes may be a pair of antibodies that recognize two different antigenic epitopes of the protein. On the other hand, for the indirect measurement where target species interact with the linker, the linker can be DNAzyme, a form of DNA oligonucleotide that could be cleaved with the presence of target species such as metal ions. In one example, to immobilize the linker-binding probes, streptavidin-coated MMPs and PMPs are used to immobilize the biotinylated probes. After immobilization, the MMPs and PMPs were rinsed three times to remove unused probes. For each washing step, the MMPs are collected using a magnetic separation rack, while the PMPs are collected using a centrifuge. For direct measurement, the target species can be directly mixed with MMPs and PMPs with gentle shaking. For indirect measurement, the target can be first mixed and react with the linker, followed by mixing with MMPs and PMPs.

Figure 4:
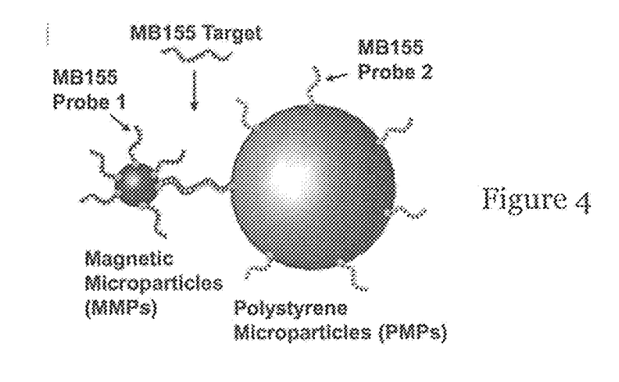
FIG. 4 is an example of the species in FIG. 2 in which the linker is a target species oligonucleoticle MB155.

FIG. 4 shows a specific target species, a target oligonucleotide, i.e. MB155, the amount of which is to be measured using the device of FIG. 1. As shown in FIG. 4, two probes of biotinylated oligonucleotides (MB155 probe 1 and probe 2) were designed with a sequence complementary to MB155 in juxtaposition. MB155 probe 1 and probe 2 were respectively immobilized onto streptavidin-coated MMPs and PMPs via a biotin-streptavidin complex. As such, when the MB55 target is present, probe 1 and probe 2 will simultaneously hybridize with the MB155 target in juxtaposition, forming a sandwich-type aggregate, MMPs-targets-PMPs. In this example, to prevent the inertial forces from breaking the linkage between MMPs and PMPs, MMPs with a diameter of 0.36 µm were selected, such that multiple MMPs can attach onto one PMP to disperse the force. The number of free PMPs trapped can be used to represent the amount of MB155 targets. In this embodiment, after rinsing, probe 1-modified MMPs and probe 2-modified PMPs were mixed with MB155, and the mixture was loaded to the inlet. As the micro-channel is hydrophilic after plasma treatment, this water-based solution would spontaneously flow towards the other end, driven by capillary force without the need for an external power source. In this example, the narrowing nozzle of the trap 106 has a minimum width of 8 µm, which can block the PMPs with a diameter of 15 µm. The depth of the PMP trapping channel was designed to be 25 µm, such that the PMPs can be accumulated as a monolayer to maximize the visible length of PMP accumulation.

Figure 5:
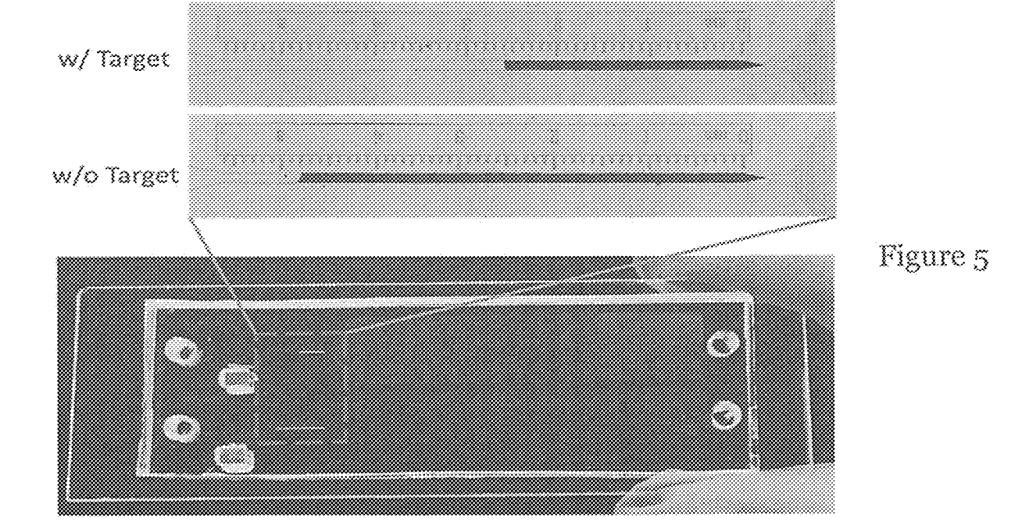
FIG. 5 is a picture showing a visual bar (upper) of a microfluidic device loaded with a sample solution with the target species of FIG. 4 and a visual bar (lower) of a microfluidic device loaded with a sample solution without the target species of FIG. 4 in one embodiment of the invention.

FIG. 5 shows a visual bar (upper) of a microfluidic device loaded with a sample solution containing the MB155 target and a visual bar (lower) of a microfluidic device loaded with a blank sample. As shown in FIG. 5, a visible bar of accumulated PMPs can be observed in the channel portion of the trap 106, and its length can be quantified using a dipstick-type ruler with reference measurement markings 108. For the blank sample, i.e., without target linkers, only MMPs were captured in the magnetic separator and all PMPs suspended in solution flow towards the channel of the trap 106, giving rise to a longer PMP accumulation length. For the sample with the MB155 target, a portion of PMPs would be retained at the site of the magnetic separator 104, and so the length of PMP accumulation is shortened.

During trapping, the water-based buffer solution can penetrate through the gap between the PMPs and the nozzle at the trap 106. Importantly, the capillary pump 110 was placed after that to ensure the capillary attraction of liquid wicking until the capillary pump 110 is fully filled, which ensures a consistent volume fill in the micro-channel and minimizes the data fluctuation between each experiment.

Figure 6A:
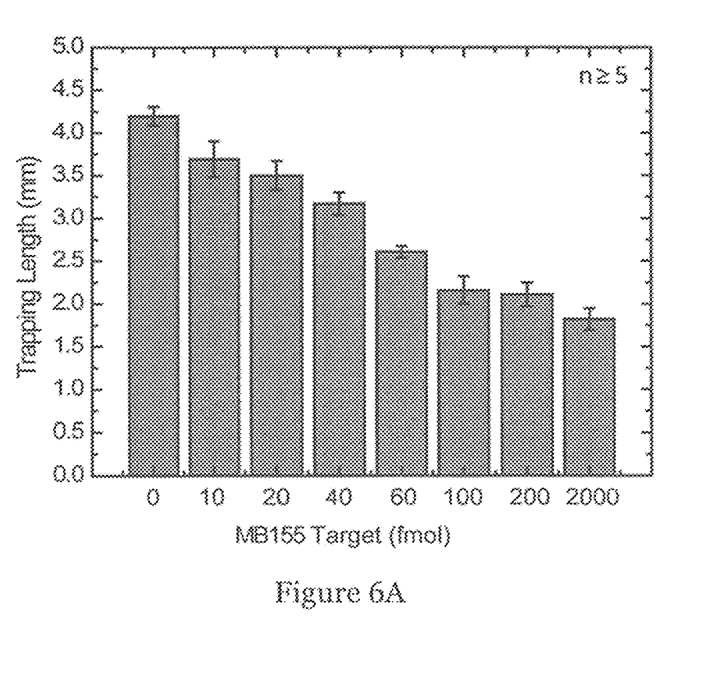
FIG. 6A is a graph showing the length (mm) of accumulated polystyrene micro-particles (PMPs) in the trap of the microfluidic device for different amount (fmol) of target species oligonucleotide MB155 (mean±SEM, n≥5)
Figure 6B:
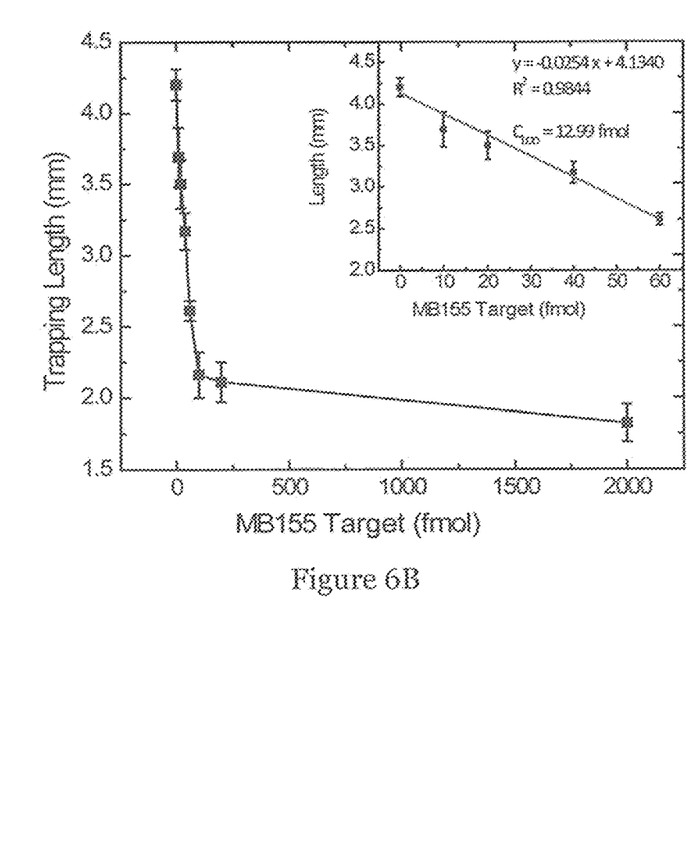
FIG. 6B is a graph showing the length (mm) of accumulated polystyrene micro-particles (PMPs) in the trap of the microfluidic device for different amount of target species oligonucleotide MB155, and which illustrates a linear relationship for 0-60 fmol target species oligonucleotide MB155 (mean±SEM, n≥5)

The limit of detection of oligonucleotides in further determined using different amount of the MB155 target, i.e. 0 mol, 10 fmol, 20 fmol, 40 fmol, 60 fmol, 100 fmol, 200 fmol and 2000 fmol in 20 µl. FIG. 6A illustrates the length of accumulated PMPs in the channel of the trap 106 for different amount of MB155 targets (which reflects the amount of free PMPs escaping from the magnetic separator). As shown, the PMP accumulation was inversely proportional to the amount of the target species. For the blank sample (0 mol), most of the PMPs can escape from the magnetic separator and accumulate in the channel of the trap 106, resulting in the longer visible bar. In contrast, when the amount of target species increases, the length of the visible bar decreases. FIG. 6B also shows the length of PMP accumulation with respect to the amount of the target species. As shown in FIG. 6B, the linear range of such change is from 0 mol to 60 fmol (inset in FIG. 6B), and the limit of detection is determined to be 13 fmol (0.65 nM in 20 µl, S/N=3, calculated on the basis of 3σ/k, where σ is the standard deviation of the blank sample, and k is the absolute slope of the linear equation, −0.0254). This demonstrates a performance comparable to that of UV/vis spectrometry.

Figure 7:
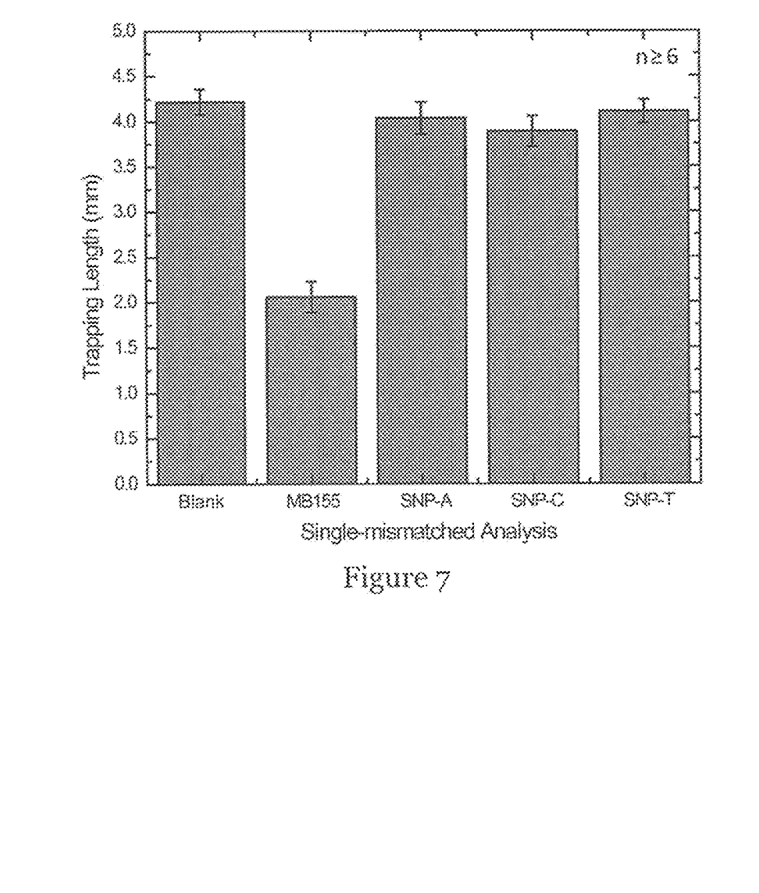
FIG. 7 is a graph showing the length (mm) of accumulated polystyrene micro-particles (PMPs) in the trap of the microfluidic device for different variations of target species oligonucleotide MB155, including no MB155, with MB155, and single-base mutated sequences SNP-A (G at the seventh base from the 5' end replaced with A), SNA-C (G at the seventh base from the 5' end replaced with C), and SNP-T (G at the seventh base from the 5' end replaced with T) (mean±SEM, n≥6)

The selectivity of detection in the micro-fluidic device 100 is also investigated using single-nucleotide polymorphisms (SNP). The selectivity is crucial for differentiating non-specific hybridization. In the test, the seventh base of the MB155 target from the 5' end, G, was replaced by A, T and C, and denoted as SNP-A, SNP-T, and SNP-C, respectively. Using 200 fmol (10 nM in 20 µl) for each case, the length of PMP accumulation shows that the results of SNP-A, SNP-T and SNP-C almost had no difference with that of the blank sample (0 mol) (around 4.20 mm in length), as shown in FIG. 7. For the MB155 target, the length was significantly shorter (2.00 mm). This shows that the microfluidic-based trap can be used for differentiating single-nucleotide polymorphisms.

Figure 8:
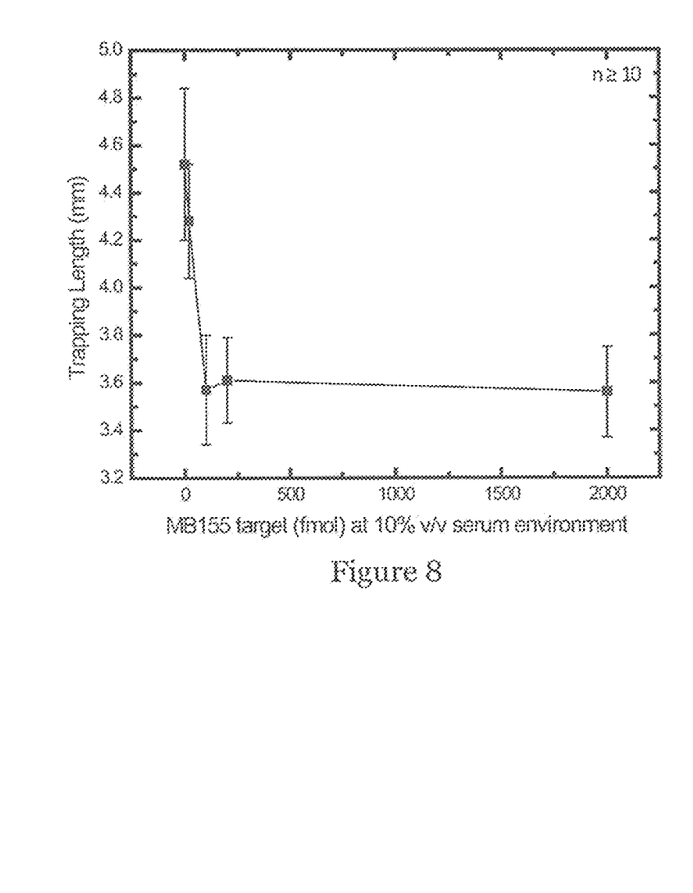
FIG. 8 is a graph showing the length (mm) of accumulated polystyrene micro-particles (PMPs) in the trap of the microfluidic device for different amount (fmol) of target species oligonucleotide MB155 at 10% v/v serum environment (mean±SEM, n≥10)

Next, the compatibility of the device 100 in the above embodiment is evaluated in a complex bio-fluid. Blood serum contains proteins, cells, RNAs, and DNase/RNase, and such interfering materials may lead to considerable challenges for hybridization and even cause failure of device functionality. To investigate the tolerance to such a complex environment, a 10% v/v serum environment containing varied amount of MB155 (0 mol, 10 fmol, 20 fmol, 40 fmol, 60 fmol, 100 fmol, 200 fmol and 2000 fmol in 20 µl) without any further pre-treatment was used. Similar to the results obtained in the buffer solution, as shown in FIG. 8, the length of PMP accumulation decreased with an increase of the target amount. While the overall length increased slightly because a small number of MMPs-targets-PMPs were carried to the trap 106 due to the high viscosity of serum, the limit of detection is around 20 fmol. This demonstrates the compatibility with a complex bio-fluid and the ability to tolerate the interfering materials in such a microfluidic device 100.

Figure 9:
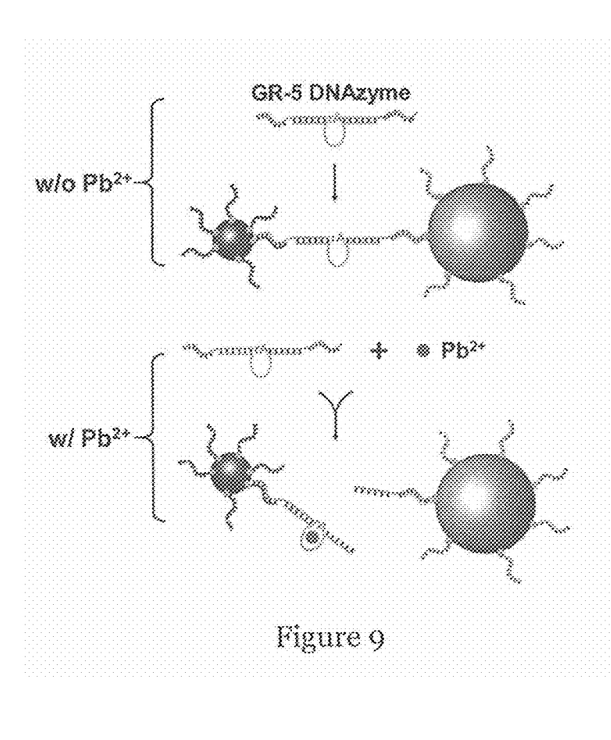
FIG. 9 is an example of the species in FIG. 2 in which the linker is a GR-5 DNAzyme arranged to be cleaved by lead ions ($Pb^{2+}$)

Based on the characterization above, a model application that uses detection of oligonucleotides for monitoring lead ions was tested. On the basis of nucleic acid hybridization, it was reported that DNAzyme, a form of DNA oligonucleotide, could catalyze a specific hydrolytic cleavage in the presence of lead ions $Pb^{2+}$. Accordingly, the target oligonucleotide MB155 is replaced with GR-5 DNAzyme, which exhibits a high selectivity towards $Pb^{2+}$. As shown in FIG. 9, the DNAzyme consists of a substrate strand GRDS and an enzyme strand GRE and the two termini of GRDS were extended and designed to be able to hybridize with MB155 probe 1 and probe 2, respectively. As such, if $Pb^{2+}$ is absent, the GR-5 DNAzyme at the amount of 200 fmol (10 nM in 20 µl) can connect MMPs and PMPs, leading to the formation of a sandwiched structure, MMPs-DNAzyme-PMPs. In contrast, when $Pb^{2+}$ is present, the ions cleave the substrate strand at the RNA site (rA) into two parts through a phosphodiester bond cleavage. This prevents the formation of the sandwiched structure MMPs-DNAzyme-PMPs and allows more PMPs to accumulate in the channel of the trap 106.

Figure 10:
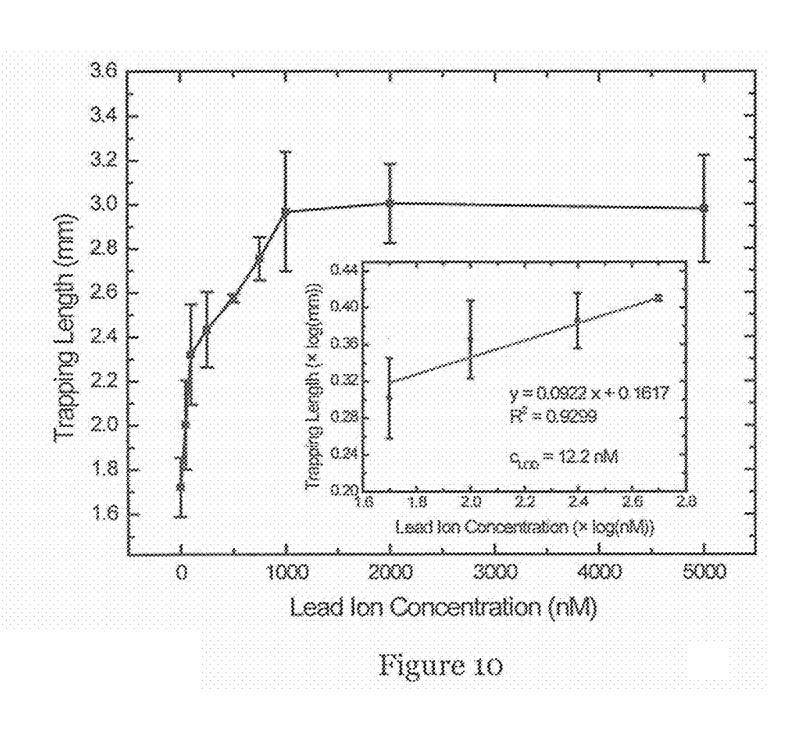
FIG. 10 is a graph showing the length (mm) of accumulated polystyrene micro-particles (PMPs) in the trap of the microfluidic device for different concentration (nM) of lead ions (mean±SEM, n≥5).

Different concentrations of $Pb^{2+}$ solution, including 0 nM, 50 nM, 100 nM, 250 nM, 500 nM, 750 nM, 1000 nM, 2000 nM and 500 nM, was tested. As expected, the trapping length due to PMP accumulation reflected the concentrations of $Pb^{2+}$ with a positive proportion, as shown in FIG. 10. Moreover, using the log scale, the linear range of such a change was from 0 to 250 nM (inset in FIG. 10), and the limit of detection can be determined to be 12.2 nM (S/N=3, calculated on the basis of 3σ/k, where σ is the standard deviation of the blank sample, and k is the absolute slope of the linear equation, 0.0922). Remarkably, the limit of detection is below the maximum human exposure to drinking water, 48 nM (10 µg l-1), according to the guideline of the World Health Organization. As such, with sufficient sensitivity and the ease of intensive sample preparation when applied in drinking/clean water, the results demonstrate a feasible application for monitoring lead ion contamination.

The above embodiments of the invention provide a simple and low-cost microfluidic platform that forms a quantitative visual bar visible by naked eyes. In the illustrated example, the detection principle is based on the changed connectivity between MMPs and PMPs. Thus, by selecting appropriate linker-binding probes, and/or combining the use of linker that reacts with the target species, the invention can be applied to various target species, such as nucleic acids, protein, metal ion, or chemical compounds. As such, the application of the invention is diverse, including inorganic chemistry, diseases diagnosis, and environmental toxin screening.

In one application, the invention can be used for the detection of disease-related biomarkers, such as nucleic acid or protein based biomarkers. Recently, nucleic acid based biomarkers have shown important for cancer diagnosis. MicroRNAs, small (~22 nt) regulatory RNAs present in blood stream due to dysfunction of cancer, was recently found its promise as tissue-based markers for cancer classification and prognostication. Thus, one embodiment of the invention can provide an effective detection of microRNAs by using it to connect MMPs and PMPs, which offers unprecedented approach to identify and evaluate the risk of cancer at early stage. Similarly, for protein-based biomarkers, by using a pair of antibodies on MMPs and PMPs that recognize two different antigenic epitopes, the presence of protein biomarkers can result in a connection between MMPs and PMPs. Malaria, for example, can be detected via *Plasmodium falciparum* histidine rich protein (Pf HRP II), the biomarker produced by malaria-causing parasite in patients' serum.

In another application, the invention can be used for environmental monitoring. Botulinum neurotoxin (BoNT) is considered one of the world's most dangerous toxins. Intoxication by BoNT may occur through the ingestion of contaminated food or from biological weapons in some undeveloped countries or military areas. Due to its toxicity, remarkable stability, and persistence in the body, a very low dose of BoNT can cause muscle paralysis or even death. To detect this species, SNAPtide can be used to connect MMPs and PMPs. SNAPtide is a short peptide designed to mimic the synaptosomal-associated protein25 (SNAP-25, a component of the trans-SNARE complex) with a site cleavable by BoNT. Thus, as an indirect measurement, the presence of BoNT would cleave the SNAPtide, causing an increase of free PMPs and longer PMP accumulation length.

In yet another application, the invention can be used for monitoring the water safety. Lead contamination in drinking water has been a serious problem worldwide because of the wide use of lead pipes in plumbing. Such contamination causes significant concerns of water safety in public health. Particularly, children with lead poisoning may suffer from slow development of childhood behaviors and permanent intellectual disability, creating significant threats to their well-being. Thus, it is highly desired to provide simple and portable platforms to every end-user for continuous monitoring of lead contamination in their domestic water source. By using DNAzyme that reacts with the lead ion to connect MMPs and PMPs, the presence of lead ion can cleave the DNAzyme, causing an increase of PMP accumulation in the trap.

Embodiments of the invention enable ready visual detection and measurement of various types of chemical and biochemical molecules, e.g. nucleic acids, protein, chemical compounds, metal ions, and thus have great potential in different applications such as portable biosensors, medical diagnosis, environmental safety, and scientific research. The invention provides a readily accessible platform ranging from disease diagnosis to monitoring of environmental toxin and metal contamination. The invention is well applicable to healthcare and environmental monitoring, especially in resource-limited settings.

Embodiments of the invention also provide various advantages. The trap, e.g., a narrowing nozzle, can trap and accumulate PMPs that form a quantitative visual bar readable by naked eyes. This provides improved convenience when compared with using a bulky reader for fluorescence or color absorbance. The accumulation of PMPs can be directly visualized and readily quantified by its length, optionally with calibration, to provide accurate result and effective measurement.

Also, the procedure of the assay in the invention is simple. The use of capillary flow promotes convenient and economical operation. The MMPs and PMPs can be modified with linker-binding probes in advance, to tailor for different applications. After mixing the sample with linker and surface-functionalized MMPs and PMPs, the only experimental procedure is to dispense the mixture into the microchip. As such, the capillary flow and magnetic attraction by permanent magnet can achieve an automated operation in a substantially power-free manner and without the need of additional instruments. There is also no need of special environment or experimental control. As a result, the requirement of experimental procedure is minimized.

Furthermore, the type of target species (the amount of which is to be measured) can be diverse. As aforementioned, the measurement can be direct, i.e. the target species can be the linker to connect MMPs and PMPs, or indirect, i.e. the target species can interact with the linker to alter connection between MMPs and PMPs. Thus, diverse types of target can be used as long as the force change is sufficient to induce different connection between MMPs and PMPs. With particular advantages for portability, energy efficiency, and user-friendly interface, embodiments of the invention can potentially revolutionize portable testing for point-of-care devices.

It will be appreciated by persons skilled in the art that numerous variations and/or modifications may be made to the invention as shown in the specific embodiments without departing from the spirit or scope of the invention as broadly described. For example, the device may be of different form, i.e., not necessarily a microchip, and made in a different scale, i.e., the device is not necessarily a microfluidic device. The separator need not be magnetic-based and instead can perform separation based on chemical or physical interactions. The shape and form of the channels can be scaled or adjusted accordingly. Different moving means can be used to move the sample solution in the channel. The number of inlets, channels, outlets, etc., can be more than one. The trap can be formed by other means, such as, for example, a filter. The device can be used with other types of sample solution, not necessarily the one with magnetic micro-particles and polymeric micro-particles. The amount of trapped species that is visible can be correlated with the amount of target species in the sample solution in any mathematical relationship, e.g., varying linearly or non-linearly. The present embodiments are, therefore, to be considered in all respects as illustrative, not restrictive.

The invention claimed is:

1. A device for visual quantification of an amount of target species in a sample solution, comprising: an inlet arranged to receive the sample solution; a separator in fluid communication with the inlet and arranged to separate one or more species from the sample solution; and a trap downstream of the separator, in fluid communication with the separator, and arranged to trap one or more species of the sample solution; wherein the trap is arranged such that the trapped species accumulates in the trap and is visible as a visual bar for determination of the amount of target species in the sample solution; wherein the trap comprises: a fluid channel that is at least partly transparent or translucent such that the trapped species is visible by naked eyes; and reference scale markings arranged along at least part of the fluid channel, where the reference scale markings are configured to provide a reference scale for the visual bar of the trapped species, and for indicating the amount of the trapped species accumulated at the trap.

2. The device of claim 1, wherein the amount of trapped species is correlated with the amount of the target species in the sample solution.

3. The device of claim 2, wherein the amount of trapped species is directly proportional to the amount of the target species in the sample solution.

4. The device of claim 2, wherein the amount of trapped species is inversely proportional to the amount of the target species in the sample solution.

5. The device of claim 1, wherein the fluid channel includes a tapered portion for trapping the one or more species.

6. The device of claim 1, further comprising a source arranged to move the sample solution towards the trap.

7. The device of claim 6, wherein the source comprises a self-driven capillary pump.

8. The device of claim 1, wherein the separator is a magnetic separator.

9. The device of claim 1, wherein the separator comprises a fluid channel with an inlet portion in fluid communication with an upstream fluid channel downstream of the inlet;

an outlet portion in fluid communication with a downstream fluid channel upstream of the trap; and a separation portion arranged between the inlet portion and the outlet portion.

10. The device of claim 9, wherein the fluid channel of the separator is curved.

11. The device of claim 9, wherein the inlet portion extends at an angle to an extension axis of the upstream fluid channel such that the separation portion is offset from the extension axis of the upstream fluid channel.

12. The device of claim 11, wherein the outlet portion extends at an angle to an extension axis of the downstream fluid channel such that the separation portion is offset from the extension axis of the downstream fluid channel.

13. The device of claim 12, wherein the extension axis of the upstream fluid channel and the extension axis of the downstream fluid channel are substantially coaxial.

14. The device of claim 9, wherein cross section of the inlet portion at least partly increases from upstream to downstream.

15. The device of claim 9, wherein cross section of the fluid channel of the separator at least partly increases from the separation portion to the outlet portion.

16. The device of claim 9, wherein the separator further comprises a magnetic element arranged at or adjacent the separation portion for attracting and thereby separating one or more species from the sample solution.

17. The device of claim 16, wherein the magnetic element comprises a permanent magnet.

18. The device of claim 1, wherein the target species include any of: nucleic acids, protein, metal ion, and chemical compounds.

19. The device of claim 1, wherein the target species include lead or lead ions.

20. The device of claim 1, wherein the device is a microfluidic device.

21. A method for visual quantification of an amount of target species in a sample solution, comprising: separating, using a separator, one or more species from the sample solution; and trapping, using a trap downstream of and in fluid communication with the separator, one or more species of the sample solution; wherein the trap is arranged such that the trapped species accumulates in the trap and is visible as a visual bar for determination of the amount of target species in the sample solution; wherein the trap comprises: a fluid channel that is at least partly transparent or translucent such that the trapped species is visible by naked eyes; and reference scale markings arranged along at least part of the fluid channel, where the reference scale markings are configured to provide a reference scale for the visual bar of the trapped species, and for indicating the amount of the trapped species accumulated at the trap.

22. A microfluidic device for visual quantification of an amount of lead ions in a sample solution, comprising; an inlet arranged to receive the sample solution; a separator in fluid communication with the inlet and arranged to separate one or more species from the sample solution; and a trap downstream of the separator, in fluid communication with the separator, and arranged to trap one or more species of the sample solution, wherein the trap is arranged such that the trapped species accumulates in the trap and is visible as a visual bar for determination of the amount of lead ions in the sample solution; wherein the trap comprises: a fluid channel that is at least partly transparent or translucent such that the trapped species is visible by naked eyes; and reference scale markings arranged along at least part of the fluid channel, where the reference scale markings are configured to provide a reference scale for the visual bar of the trapped species, and for indicating the amount of the trapped species accumulated at the trap.

* * * * *